(12) United States Patent
Edens et al.

(10) Patent No.: US 6,521,190 B1
(45) Date of Patent: Feb. 18, 2003

(54) CELL COLLECTION APPARATUS

(75) Inventors: Carl Ted Edens, Ellicott City, MD (US); Julia Brill, Erlangen (DE)

(73) Assignee: Digene Corporation, Gaithersburg, MD (US)

( * ) Notice: Subject to any disclaimer, the term of this patent is extended or adjusted under 35 U.S.C. 154(b) by 0 days.

(21) Appl. No.: 09/574,320

(22) Filed: May 19, 2000

(51) Int. Cl.[7] .................................................. B01L 3/00
(52) U.S. Cl. ................... 422/102; 422/104; 435/307.1; 435/308.1; 435/309.1
(58) Field of Search .................. 435/307.1, 308.1, 435/309.1, 283.1, 284.1, 288.1, 288.2, 299.2, 304.1, 304.2, 304.3; 422/102, 104, 99; D24/224; 436/309.1, 308.1, 292, 294, 295, 296, 312, 316, 809, 810; 600/569; 220/2.112, 4.21, 4.22, 4.23, 500

(56) References Cited

U.S. PATENT DOCUMENTS

| | | | | |
|---|---|---|---|---|
| 2,288,065 A | * | 6/1942 | Benotti | ....................... 422/102 |
| 3,604,067 A | * | 9/1971 | Brown | ........................ 24/67 R |
| 4,706,342 A | * | 11/1987 | Yu | ............................... 24/67.9 |
| 4,927,764 A | * | 5/1990 | Lyman et al. | .................. 215/10 |
| 4,949,864 A | * | 8/1990 | LaKier | ..................... 15/257.05 |
| 5,112,957 A | * | 5/1992 | Pollard | ........................ 204/462 |
| 5,139,952 A | * | 8/1992 | Honda et al. | ............... 422/102 |
| 5,370,128 A | | 12/1994 | Wainwright | |
| 5,422,273 A | * | 6/1995 | Garrison et al. | .......... 435/307.1 |
| 5,783,440 A | * | 7/1998 | Stevens | ....................... 215/386 |
| 5,871,700 A | * | 2/1999 | Konrad | ........................ 422/102 |
| 6,194,199 B1 | * | 2/2001 | Asa | .......................... 435/309.1 |

FOREIGN PATENT DOCUMENTS

JP                02114163 A   *   4/1990

\* cited by examiner

Primary Examiner—Jill Warden
Assistant Examiner—Yelena Gakh
(74) Attorney, Agent, or Firm—Morgan & Finnegan, LLP

(57) ABSTRACT

This invention provides a novel apparatus for obtaining a cellular or tissue sample from a brush device. The apparatus comprises a collection container including an open end and a closed end, and an interior wall. One portion of the interior wall defines a central axis. Another portion of the interior wall is capable of holding a brush device at an angle with respect to the central axis.

13 Claims, 3 Drawing Sheets

CELL COLLECTION APPARATUS

FIELD OF INVENTION

The present invention relates generally to the collection of cellular samples and, more particularly, to a collection apparatus for efficient access and collection of cellular samples from a cytology brush device.

BACKGROUND OF THE INVENTION

The diagnosis and detection of cell or tissue samples are vital in the prevention and treatment of precancerous and cancerous lesions, or other diseases. Cytology slides are usually prepared to screen and diagnose cellular samples taken from, for example, tissue samples, samples from the uterine cervix, sputum, urethral, bronchial brushings and washings, and other body fluids. Tests used for detecting infections by molecular or immunoassay based technologies also depend on these types of samples and sampling devices. The reliability of the sample obtained, however, is a primary issue.

Due to the typically serious nature of the disease that a doctor is attempting to detect, it is critical that the cell or tissue samples are completely and accurately transferred from the retrieving instrument (i.e. cytology brush device) to the testing medium. Inaccurate retrieval of the cell or tissue sample could possibly result in an inaccurate or delayed diagnosis and even the misdiagnosis of a serious medical condition.

One of the most common uses of cytology slides is for screening and diagnosis of a cervical sample. Carcinoma of the cervix is one of the most common malignancies in women, causing nearly 5,000 deaths per year in the United States. Approximately 60% of these cases are associated with absent or deficient screening. Approximately 25% of the screening failures are the result of errors in cervical sampling or smear interpretation. Saway, George F. (M.D.), Grimes, David A. (M.D.), "New Technologies in Cervical Screening: A Word Of Caution", Obstetrics and Gynecology, 1999, Vol. 94, pg. 1, which is incorporated herein by reference.

Cervical sampling traditionally involves microscopic assessment of cervical Papanicolaou smears, called Pap smears. This traditional method for cervical sampling requires scraping a woman's cervix with a sampling device, such as a cytology brush device, and smearing this sample onto a slide for review by a medical lab professional. The specimen is gently spread across a slide to evenly distribute the cell sample. The slide is then fixed, stained, and examined under a light microscope for cellular abnormalities.

It is, however, difficult to always get a representative sample because a large portion of the cell sample is lodged within the bristles of the cytology brush device making it difficult to transfer all of the cells to a slide by merely wiping the bristles against the smooth slide surface. Thus, valuable diagnostic material is potentially lost, increasing the risk of an erroneous diagnosis.

Furthermore, due to the shape of the brush (i.e. spiral shaped), the cells can be transferred to the slide only by wiping, rubbing or rotating the brush against the slide surface. To transfer even a portion of the cells from this type of brush takes excess time and care. Thus, insufficient cell transfer can be very common when this type of brush and cell transfer method is used.

A variety of technologies or clinical strategies, such as liquid-based cytology systems, have been developed to improve Pap testing. For example, the Cytyc, Inc. (Marlborough, M.A.), ThinPrep® and the TriPath, Inc. (Burlington, N.C.), CytoRich® Pap test systems are two commercially available, FDA approved fluid-based methods used for the collection and preparation of cervicovaginal samples.

However, in the liquid-based cytology technique, the accuracy of the resulting sample is again dependent on the successful and complete transfer of the cell samples disposed on the bristles of the cytology brush device to the fixative solution within the container. Typically, this transfer is done by placing the bristled end of the cytology brush device within the container holding the solution. The brush is then manually vortexed within the fixative solution in an attempt to dislodge all of the cells from the bristles. However, the vortexing action within the fixative solution alone is often insufficient to dislodge or flush out all of the cells that are contained on or within the bristles. Again, the disadvantage is that all of the cell sample is not transferred to the fixative solution, resulting in the same problems as discussed above.

A separate technical issue that is problematic when applying cytology brush devices to automated robotic systems is that the shaft of the brush device can interfere with the pipette tips of an automated pipettor. This can actually cause errors in sampling for assays utilizing automation, such as, for example, the Hybrid Capture® molecular based tests for HPV chlamydia and gonorrhea, by Digene Corporation (Gaithersburg, Md.).

SUMMARY OF THE INVENTION

The present invention provides an apparatus that overcomes these problems. A collection apparatus according to one embodiment of the present invention comprises a collection container. The collection container includes an open end and a closed end. A first interior portion of the container at the open end defines a central axis. A second interior portion of the container at the closed end is capable of holding the bristle end of a brush device having a body of bristles on a shaft so that the shaft is angled with respect to the central axis of the first interior portion of the container.

In alternate embodiments, a device including a restricting member is used with a standard collection apparatus to angle the shaft of the brush device from the central axis defined by the first interior portion of the collection apparatus. This device can also be used with the first embodiment described above.

DETAILED DESCRIPTION OF THE PREFERRED EMBODIMENTS

Hereinafter, the invention will be described in greater detail with reference to the preferred embodiments. However, it is understood that the apparatus is applicable for the collection of any sample, preferably clinical cellular samples, known in the art.

Figure 2:
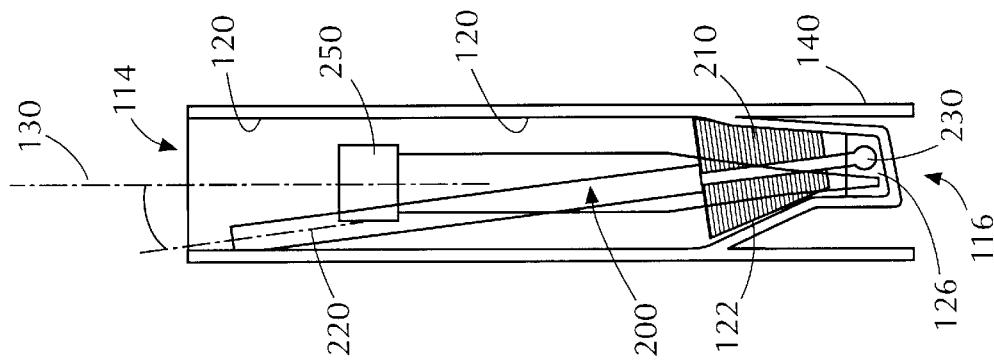
FIG. 2 is a cross-sectional view of one embodiment of the present invention of how second interior portion 122 holds shaft 220 of a cytology brush device at an angle with respect to central axis 130 permitting a cell sample to be removed from the cell collection apparatus of the present invention with a pipette type device.

A brush device 200 for taking samples of cells from, for example, the cervix, generally consist of a conical body 210 of bristles on a shaft or rod 220 which serves as a handle when taking samples and a tip 230 (FIG. 2). The lateral surface of the conical body 210 of bristles can be straight or concave along a circular arc.

Figure 1A:
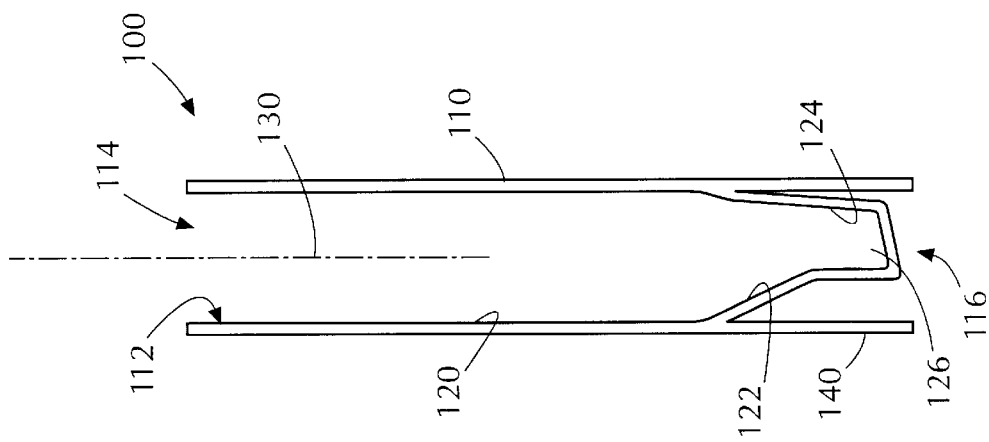
FIG. 1A is a longitudinal cross-sectional view illustrating three interior portions of a cell collection apparatus of one embodiment of the present invention.

Referring now to FIG. 1A, in one embodiment of the invention, a collection apparatus 100 for efficient access and collection of cellular samples is illustrated. The collection apparatus 100 includes a collection container 110 including an open end 114, a closed end 116, and an interior wall 112.

The interior wall 112 of the collection container 110 defines three interior, portions 120, 122, and 124. The first interior portion 120 extends from the open end 114 and has a horizontal cross-section forming a substantially circular shape, although the first interior portion 120 can have a horizontal cross-section formed into any other shape, such as, for example, elliptical, square, polygonal, or the like. The first interior portion 120 defines a first central axis 130 passing trough the center of the open end 114. The interior wall 112 extends from the first interior portion 120 and angles inwardly to form the second interior portion 122. The walls of the second interior portion 122 angle inwardly as they extend from the first interior portion 120 so that the cross sectional area of the second interior portion 122 decreases as it extends away from the first interior section 120 forming an inverted truncated conical shape. The second interior portion 122 defines a second central axis. The second interior portion 122 is oriented and extends from the first interior portion 120 so that the central axis of the second interior portion, the second central axis, (shown by the axis of the brush shaft 220) is at an oblique angle with respect to the central axis 130 of the first interior portion 120, the first central axis. The angled relationship serves to hold the brush shaft at an angle with respect to the first central axis. Although, by example, a conical shape is described above, the second interior portion 122 can also be other shapes, such as, for example, an inverted oblique truncated pyramid or any other multiple sided shape having slanted walls or the like, capable of holding the bristle end of a brush device so that the shaft is angled with respect to the central axis of the first interior portion 120. The third interior portion 124 extends from the second portion 122 to form a recess 126 at the closed end 116 of the collection container 110. The first, second and third interior portions 120, 122, 124 are arranged so that there is an unencumbered straight path from the open end 114 to the recess 126 for entry of a pipette.

As shown in FIG. 2, the wall of the second interior portion 122 is formed to hold the cytology brush device 200 at an angle with respect to the central axis 130 of the first interior portion 120 of the collection container 110 so that the shaft or rod 220 is angled with respect to the central axis 130.

Figure 1B:
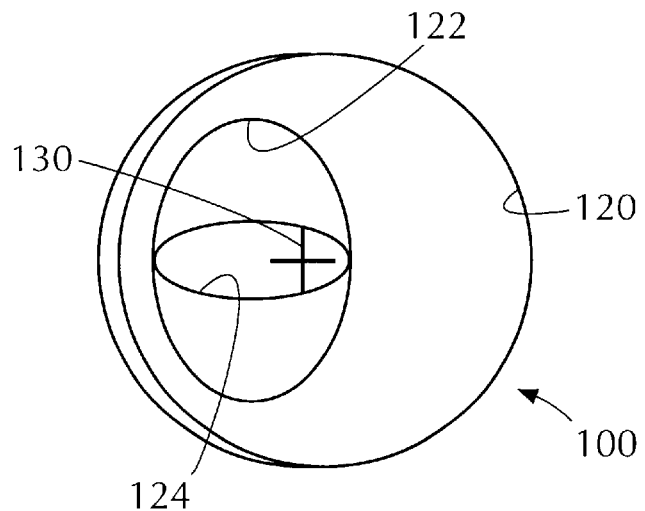
FIG. 1B is a top view illustrating the horizontal cross-section of the second interior portion of a cell collection apparatus of one embodiment of the present invention.

As illustrated in FIGS. 1B and 2, the second interior portion 122 forms a substantially, elliptical horizontal cross-section. The second interior portion 122 has an elliptical horizontal cross-section shaped so as to promote fluid flow through the bristles when the container is agitated with an orbital motion. In addition, the elliptical shape of the horizontal cross-section of the second interior portion 122 is designed to promote improved flow of the specimen medium around the bristles of the brush device and improve the elution of the cells and tissues from the brush device.

The recess 126 formed by the third interior portion 124 is provided at the bottom of the collection container 110 to house the tip 230 of the cytology brush device 200. The outer periphery of the container extends to a point below the third interior portion 124 thereby forming a base 140 upon which the container 110 can stand.

By angling the shaft or rod 220 of the cytology brush device 200, unencumbered access to the specimen by use of specimen withdrawing instrument 250, such as, for example, a pipette, is permitted. Angling the shaft 220 also enables a robotic pipetting system to insert a pipette vertically without interference from the brush shaft 220. This prevents the withdrawing instrument 250 from hitting, jamming on, or interfering with the top or shaft 220 of the cytology brush device 200.

In collection apparatus 100 may be made from a clear, polypropylene material that is inert with respect to various alcohol fixative solutions, although it will be appreciated that a variety of other materials, such as, for example, glass or other clear or plastic materials, may be used.

A cellular sample is typically obtained from the cervix by gently inserting the cytology brush device 200 until only the bristles closest to the shaft or rod 220 are exposed to the cervical tissue. The brush device 200 is then slowly rotated and removed.

The cytology brush device 200 containing the cell or tissue sample from a human or animal subject is preferably placed in any liquid-based cytology medium used and known in the art. One example of such a cytology medium is known as a Universal Collection Medium (UCM) from Digene Corp. (Gaithersburg, Md.). UCM is a cell collection medium which preserves both cell morphology and cellular biomolecules for quantitative analysis in a cell sample so that multiple assays can be carried out from a single patient sample. Further information about the UCM is set forth in PCT International Application No. PCT/US98/26342 (European patent application number 98962066.1), filed on Dec. 11, 1998 by Attila T. Lorincz and Yanlin Tang for a Universal Collection Medium which is incorporated herein by reference. Other liquid-based cytology media known in the art can be used, such as, for example, PreservCyt® from Cytyc, Inc. (Boxborough, Mass.) and CytoRich® Preservative Fluid from TriPath, Inc. (Burlington, N.C.).

The wall of the second interior portion 120 of the collection container 110 holds the cytology brush device 200 while the specimen collection medium is being mixed or vortexed. As During mixing or vortexing, the bristles 210 of the cytology brush device 200 are agitated by the specimen collection medium. The bristles 210 can be sufficiently agitated as the medium flows around and through the bristles 210 so that the cell or tissue samples are dislodged from or flushed out of the bristles 210 and become suspended within the specimen collection medium. In this manner, a more representative sample is retrieved and evaluated.

Figure 3B:
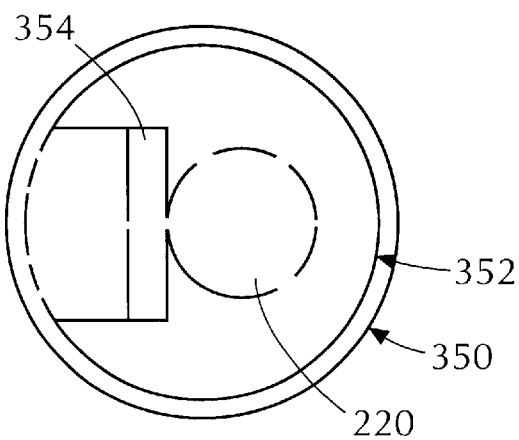
FIG. 3B is a top view of the insert 350 of FIG. 3A.
Figure 3A:
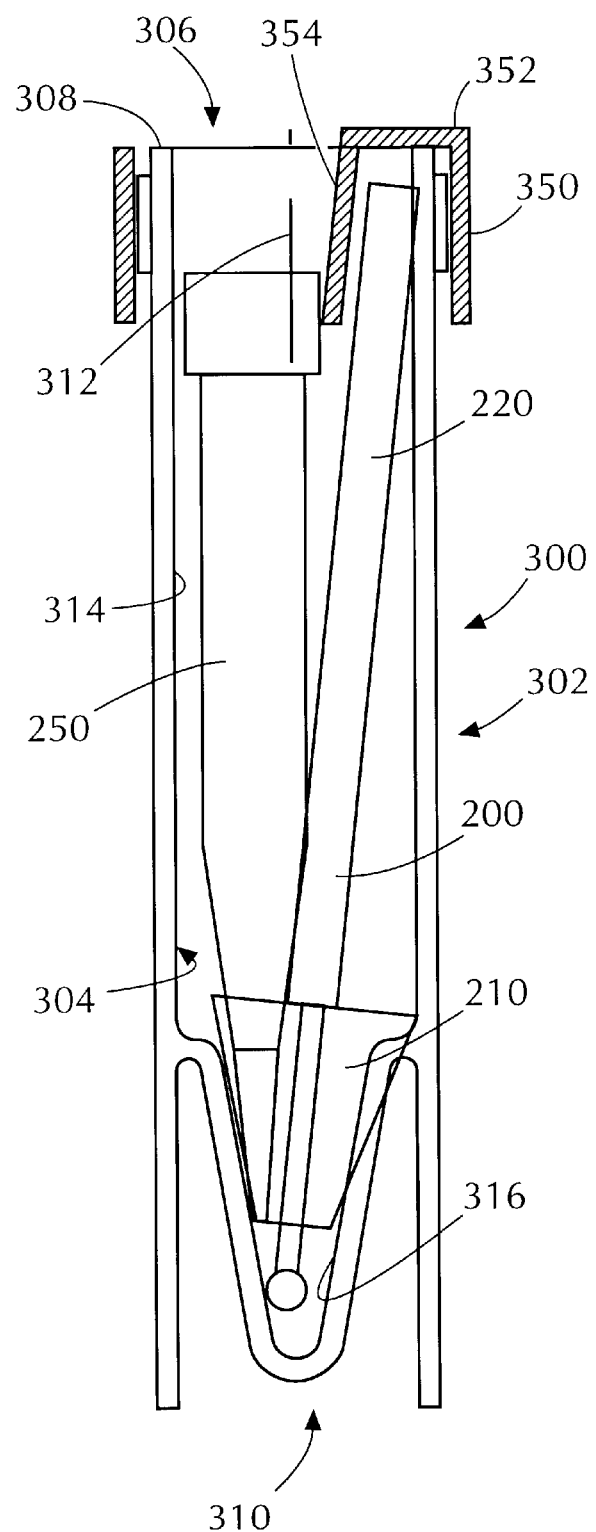
FIG. 3A. is a cross-sectional view illustrating the restricting member 354 of the insert 350 of one embodiment of the present invention holding shaft 220 of the cytology brush device at an angle with respect to central axis 312 permitting a cell sample to be removed from the cell collection apparatus of the present invention with a pipette type device.

In an alternate embodiment, as illustrated in FIG. 3A, the shaft of the cytology brush device does not interfere with the insertion of a specimen withdrawing instrument, such as, for example, a pipette, into a standard collection apparatus by an insert. As shown in FIG. 3A, a standard collection apparatus 300 typically includes a collection container 302 having an interior wall 304, an open end 306 having a lip 308, a closed end 310, and a central axis 312. The interior wall 304 of the collection container 302 includes two interior portions 314, 316. The first interior portion 314 has a horizontal cross-section formed into a substantially, circular shape and extends from the open end 306 to form a cylindrical section. Extending from the first interior portion 306 is an inverted conically shaped second interior portion 316 with its apex forming the closed end 310 having a rounded bottom.

The insert 350 is fit onto the lip 308 of the open end 306 of the container 302 in, for example, a friction tight manner. The insert 350 has a circular clip portion and an inwardly extending rim 352 formed around the perimeter of the top end of the clip portion. The inwardly extending rim 352 is wider than the interior diameter of the collection container 302 at the open end 306 and thus acts to prevent the insert 350 from being inserted within the container 302 beyond the point of the rim 352.

The insert 350 includes a restricting member 354 projecting from the rim 352 into the container 302. While positioned on the container 302, the restricting member 354 projects from the rim 352 towards the central axis 312 of the first interior portion 314 of the collection container 302. The restricting member 354 is constructed so as to confine the shaft or rod 220 of the cytology brush device 200 at an angle with, and away from, the central axis 312 of the collection container 302. Thus, as illustrated in FIGS. 3A and 3B, the shaft or rod 220 of the cytology brush device 200 is restricted by the restricting member 354 of the insert 350 from interfering with the insertion and removal of the specimen withdrawing instrument 250, such as, for example, pipette, as a specimen is obtained and withdrawn from the collection container 302.

The insert 350 may be made of a single piece of resilient material, such as, for example, polypropylene or other resilient plastics which are capable of holding the shaft 220 of the brush device 200 away from the central axis 130 of the first interior portion 120. The material should be inert with respect to various alcohol fixative solutions. It will be appreciated that a variety of other materials may also be used.

The insert 350 can also be used with the collection container 110 described in relation to the embodiments illustrated in FIGS. 1 and 2. In this embodiment, the restricting member 354 is used to assist the second interior portion 122 to angle the shaft away from the central axis 130 of the first interior portion 120.

It will be apparent to those skilled in the art that various modifications and variations can be made in the apparatus of the present invention without departing from the spirit or scope of the invention. Thus, it is intended that the present invention embraces all such modifications and variations within the spirit and scope of the appended claims.

What is claimed is:

1. A collection apparatus comprising a collection container comprising a first interior portion, second interior portion and third interior portion, wherein the first interior portion of the container extends from an open end to the second interior portion and defines a first central axis;

the second interior portion extends inwardly and has a decreasing cross-sectional area from the first interior portion to the third interior portion, and defines a second central axis at an oblique angle with respect to the first central axis, the second interior portion being sized to engage bristles of a brush device having a body of bristles on a shaft and to urge the shaft of the brush device at an angle with respect to the first central axis;

the third interior portion extends from the second interior portion and defines a closed end; and the first, second and third interior portions are sized and arranged to form an unencumbered straight line path from the open end to the closed end of the collection container.

2. The apparatus of claim 1, wherein the first interior portion of the container has a horizontal cross-section that is circular in shape.

3. The apparatus of claim 1, wherein the second interior portion of the container forms an inverted conical shape.

4. The apparatus of claim 1, wherein the second interior portion of the container has a horizontal cross-section that is elliptical.

5. The apparatus of claim 1, wherein the container contains a specimen collection medium that is used for the retrieval of cell samples.

6. The apparatus of claim 1, wherein the third interior portion forms a recess at the closed end of the container.

7. The apparatus of claim 1, further comprising a removeable insert for the container, wherein said container has a lip at the open end, the insert includes a rim which fits on the lip of the open end of the container and a restricting member projecting from the rim to hold the shaft of the brush device away from the central axis of the container.

8. A removeable insert for a tube having an open end with a lip, a closed end, and a central axis, the removable insert comprising: a circular clip portion that attaches to the perimeter of the tube lip, a rim attached to the clip portion and extending into the open end of the tube, and a restricting member attached to the rim and extending downwardly into the tube, the restricting member restraining a shaft of a brush against a wall of the tube and away from the central axis of the tube.

9. The removable insert of claim 8, wherein the insert is held to the lip of the open end of the tube in a friction tight manner.

10. A collection apparatus comprising:

a collection container including an open end having a lip and a closed end, wherein a first interior portion of the container at the open end defines a central axis, and wherein a second interior portion of the container at the closed end is capable of holding a brush device having a body of bristles on a shaft such that the second interior portion of the container has a horizontal cross-section that is elliptical so that the shaft of the brush device is angled with respect to the central axis of the first interior portion of the container for allowing fluid flow dislodgment of a specimen on the brush device and unencumbered access to the closed end; and a removeable insert for the collection container, wherein the insert includes a restricting member which fits on the lip of the open end of the collection container and holds the shaft of the brush device away from the central axis of the collection container.

11. A collection apparatus comprising:

a collection container including an open end having a lip and a closed end, wherein a first interior portion of the container at the open end defines a central axis, and wherein a second interior portion of the container at the closed end is capable of holding a brush device having a body of bristles on a shaft such that the second interior portion has a wall angled with respect to the central axis for the brush device to rest so that the shaft of the brush device is angled with respect to the central axis of the first interior portion of the container for allowing fluid flow dislodgment of a specimen on the brush device and unencumbered access to the closed end; and a removeable insert for the collection container, wherein the insert includes a restricting member which fits on the lip of the open end of the collection container and holds the shaft of the brush device away from the central axis of the collection container.

12. A collection apparatus comprising:

a collection container including an open end having a lip and a closed end, wherein a first interior portion of the container at the open end defines a central axis, and wherein a second interior portion of the container at the closed end is capable of holding a brush device having a body of bristles on a shaft such that the second interior portion of the container has a horizontal cross-section that is elliptical and the second interior portion further includes a wall angled with respect to the central axis for the brush device to rest so that the shaft of the brush device is angled with respect to the central axis of the first interior portion of the container for allowing fluid flow dislodgment of a specimen on the brush device and unencumbered access to the closed end; and a removeable insert for the collection container, wherein the insert includes a restricting member which fits on the lip of the open end of the collection container and holds the shaft of the brush device away from the central axis of the collection container.

13. The collection container of claim 1 wherein the first central axis extends from the open end through the closed end without impinging upon the interior wall.

* * * * *